United States Patent
Huang

(10) Patent No.: US 6,782,919 B2
(45) Date of Patent: Aug. 31, 2004

(54) REVOLVING VALVE FOR AN OXYGEN MACHINE

(76) Inventor: Shao Shih Huang, 5F, No. 9, Lane 180, Tong Hua St., Da Ann Dist., Taipei (TW)

( * ) Notice: Subject to any disclaimer, the term of this patent is extended or adjusted under 35 U.S.C. 154(b) by 0 days.

(21) Appl. No.: 10/352,976

(22) Filed: Jan. 29, 2003

(65) Prior Publication Data

US 2004/0144430 A1 Jul. 29, 2004

(51) Int. Cl.⁷ .............................................. F16K 31/04
(52) U.S. Cl. .................. 137/624.13; 137/862; 137/870; 137/876; 137/887
(58) Field of Search ........................ 137/624.13, 627.5, 137/872, 876, 887, 870, 861, 862

(56) References Cited

U.S. PATENT DOCUMENTS

| | | | | |
|---|---|---|---|---|
| 2,367,319 A | * | 1/1945 | Wahlberg | 137/624.13 |
| 3,092,073 A | * | 6/1963 | Conde | 137/624.13 |
| 4,190,082 A | * | 2/1980 | Crespo | 137/872 |
| 4,787,417 A | * | 11/1988 | Windsor | 137/624.13 |
| 5,353,838 A | * | 10/1994 | Grant | 137/624.13 |
| 5,368,072 A | * | 11/1994 | Cote | 137/872 |

* cited by examiner

*Primary Examiner*—Kevin Lee
(74) *Attorney, Agent, or Firm*—Rosenberg, Klein & Lee

(57) ABSTRACT

A revolving valve for an oxygen machine includes a motor, a cage, a motor secured in the cage, a valve linking to the motor and an air box secured on top of the cage. The valve has a semicircular recess. The air box comprises an air inlet on the top. The air box further comprises a main air passage, a main air outlet, a first secondary air passage, a first secondary air inlet, a second secondary air passage, and a second secondary air inlet, and they all are totally isolated from each other. The first secondary air inlet and the second secondary air inlet are next to the main air outlet. When the motor drives the valve to turn, the recess conducts the first secondary air inlet and the second secondary air inlet with the main air outlet in sequence.

1 Claim, 10 Drawing Sheets

REVOLVING VALVE FOR AN OXYGEN MACHINE

FIELD OF THE INVENTION

This invention relates to a revolving valve for an oxygen machine, and more particularly, to a revolving valve to provide a constant fresh air supply.

BACKGROUND OF THE INVENTION

There are various oxygen machines used by hospitals for medical purposes. The principle of the oxygen machine is to suck air through a filter to obtain oxygen and output through the machine.

Most of the machines use electromagnetic valves to control air inlet and to expel other gas and output oxygen. These electromagnetic valves are controlled by a circuit system, which are complicated and require frequent maintenance. That is not cost effectiveness.

SUMMARY OF THE INVENTION

It is the primary object of the present invention to provide a revolving valve for an oxygen machine, which maintains a constant oxygen output.

It is another object of the present invention to provide a revolving valve for an oxygen machine, which design is simple and is cost effectiveness.

It is a further object of the present invention to provide a revolving valve for an oxygen machine, which is easy to maintain and is more reliable.

DETAILED DESCRIPTION OF THE PREFERRED EMBODIMENT

Figure 1:
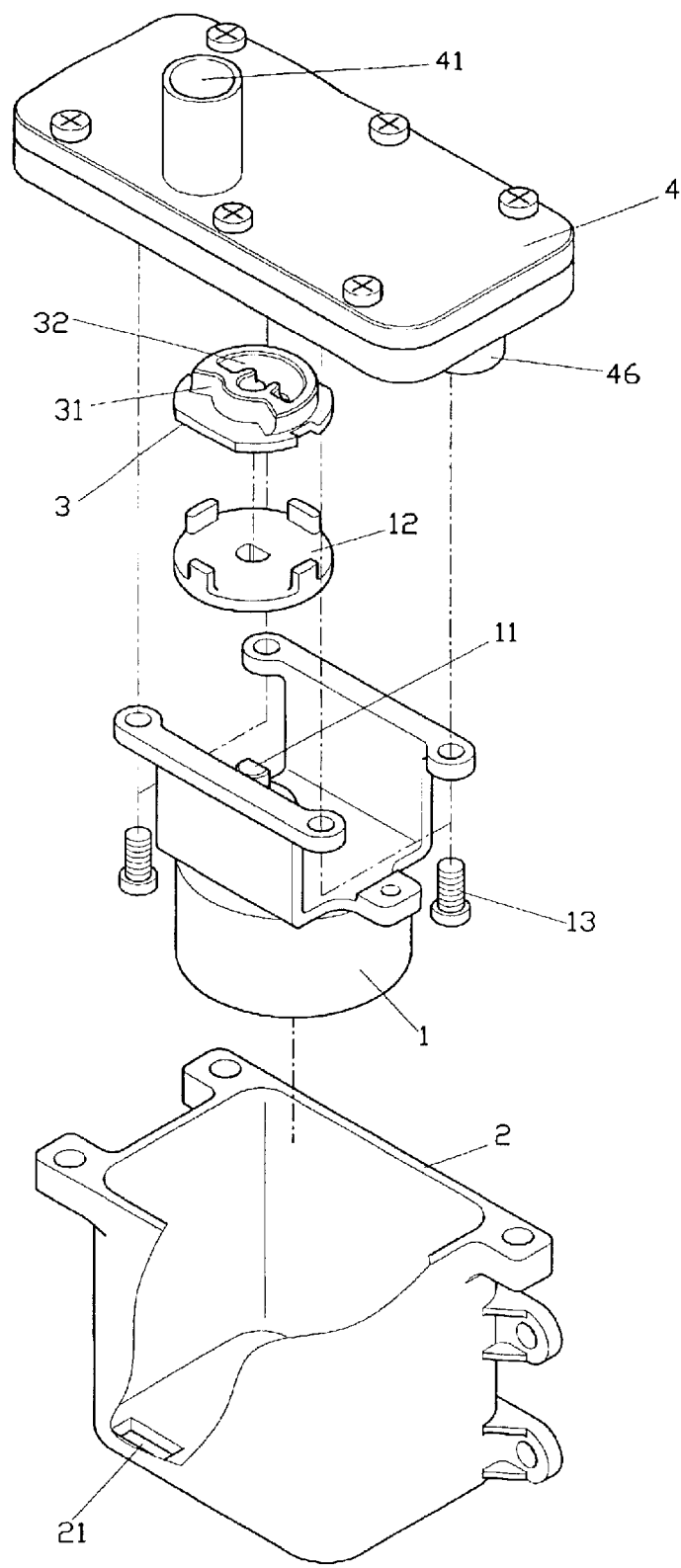
FIG. 1 is an exploded view of the present invention.
Figure 2:
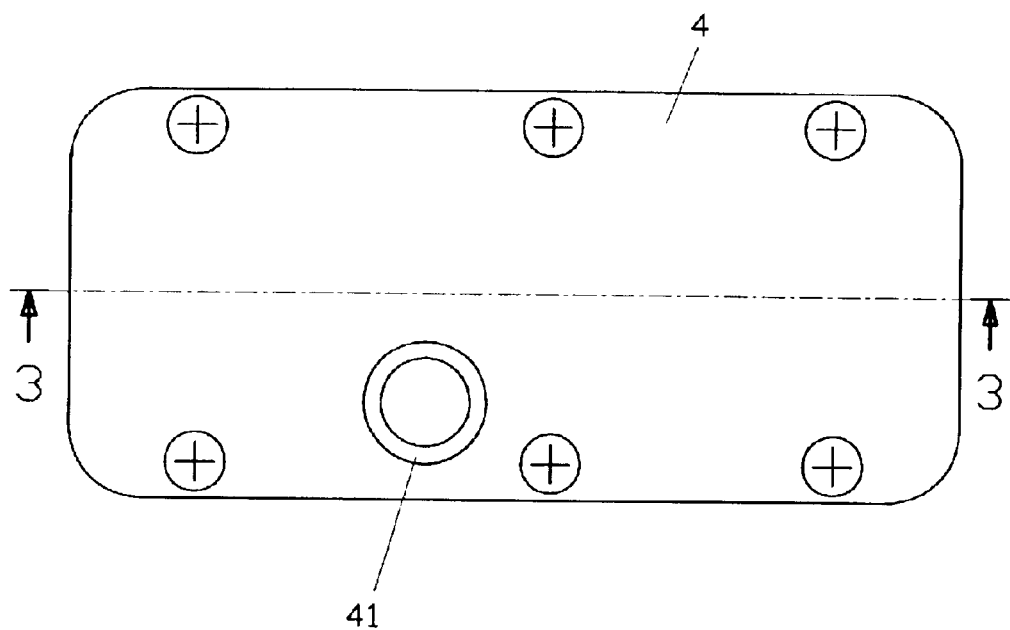
FIG. 2 is a top view of the present invention.

A revolving valve for an oxygen machine, as shown in FIGS. 1~4, comprises a motor 1, a cage 2, a valve 3 and an air box 4.

The motor 1 has a driving shaft 11 connected to a driven disc 12, which in turn drives the valve 3 and is secured underneath the air box 4 with bolts 13.

The cage 2 has an air outlet 21. The motor 1 is secured in the cage 2. The top of the cage 2 is secured with the air box 4.

The valve 3 has a sealed rib 31 with a recess 32 inwardly in a semicircular shape.

Figure 3:
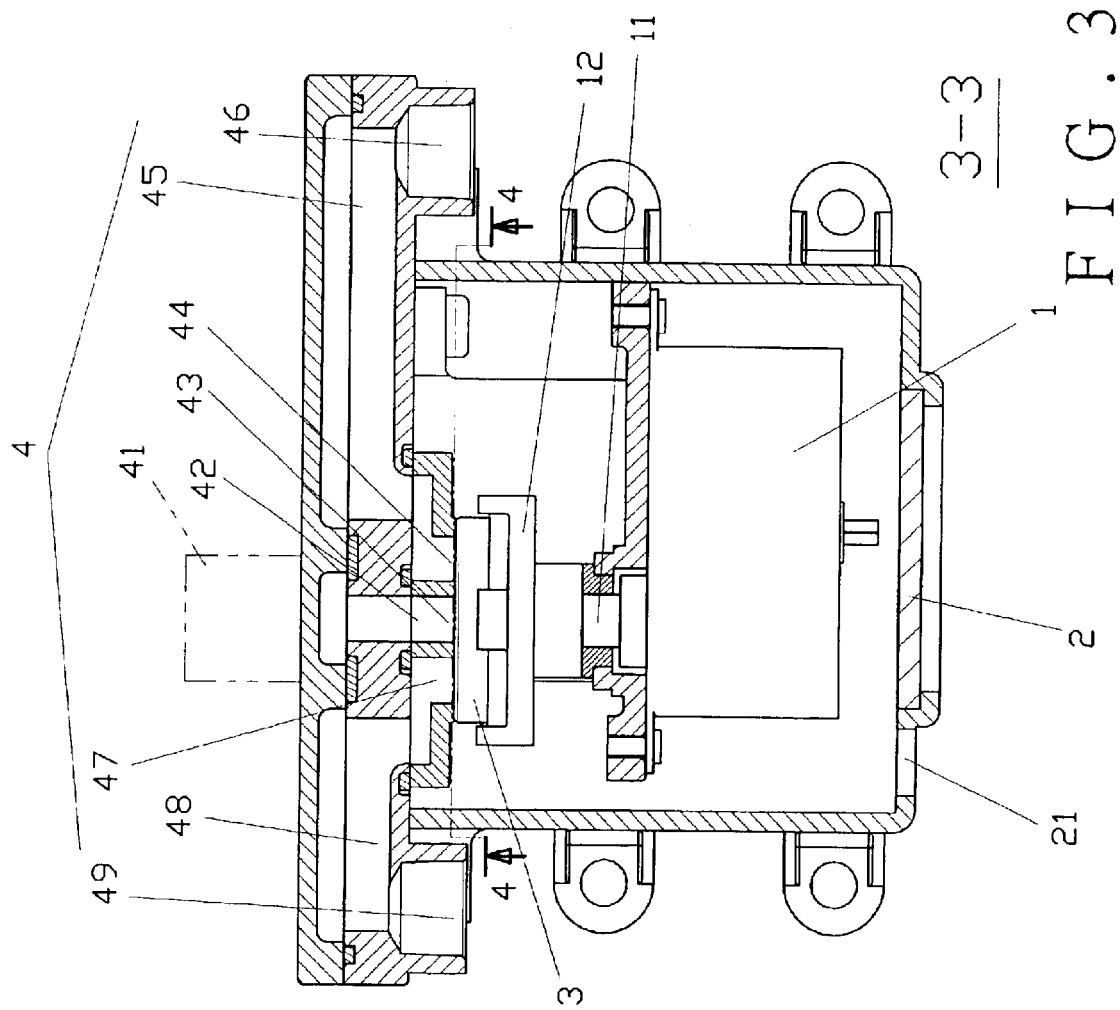
FIG. 3 is a view taken along line 3—3 of FIG. 2.
Figure 4:
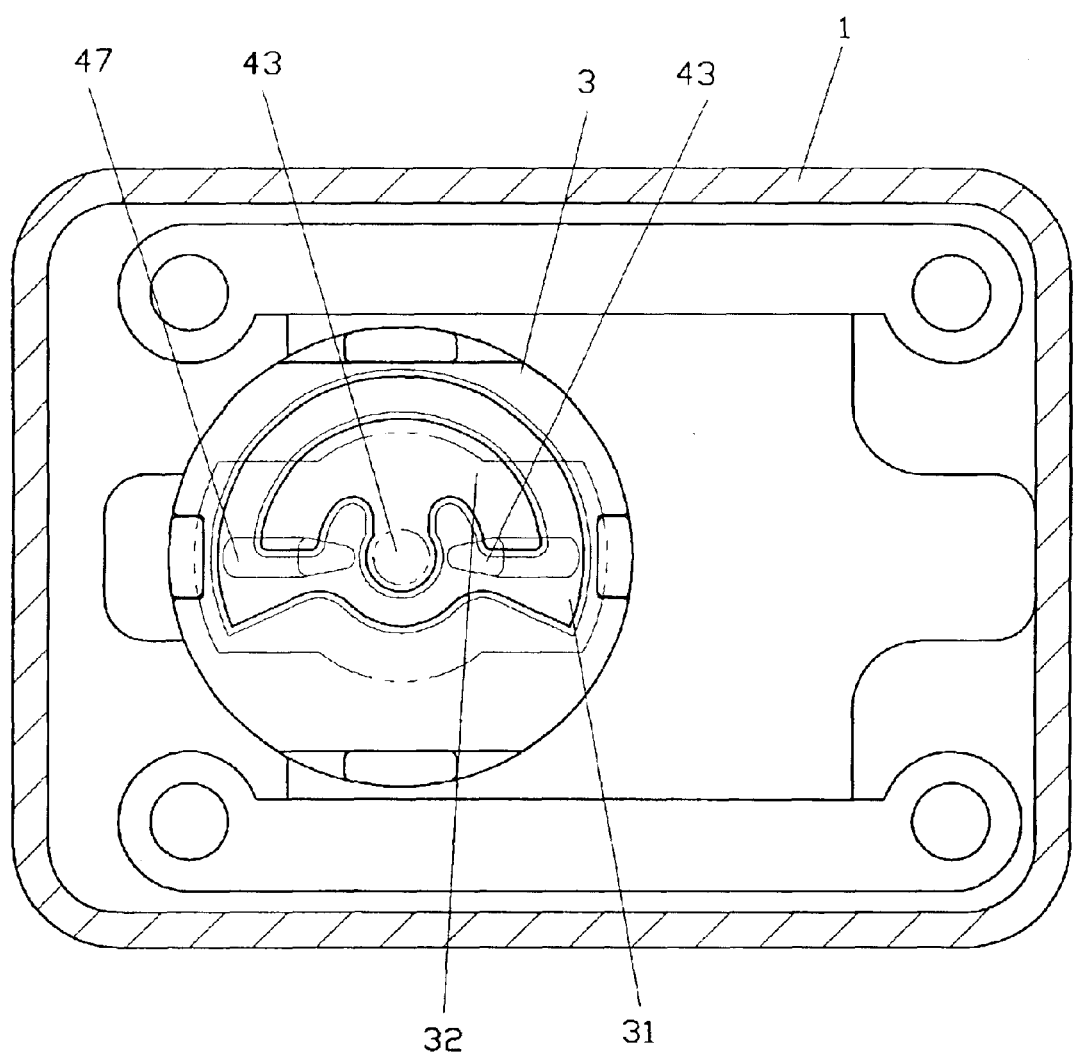
FIG. 4 is a view taken along line 4—4 of FIG. 3.

As shown in FIG. 3, the air box 4 comprises a main air inlet 41, a main air passage 42, a main air outlet 43, a first secondary air inlet 44, a first secondary air passage 45, a first secondary air outlet 46, a second secondary air inlet 47, a second secondary air passage 48, and a second secondary air outlet 49. The main air passage 42, the first secondary air passage 45 and the second secondary air passage 48 within the air box 4 are totally isolated from each other. The main air inlet 41, the main air passage 42 and the main air outlet 43 are interconnected with each other. The main air inlet 41 is located on one side of the air box 4, and the main air outlet 43 is on the other side thereof. The first secondary air inlet 44, the first secondary air passage 45, and the first secondary air outlet 46 are interconnected with each other. The second secondary air inlet 47, the second secondary air passage 48, and the second secondary air outlet 49 are interconnected with each other. The first secondary air inlet 44, the first secondary air outlet 46, the second secondary air inlet 47 and the second secondary air outlet 49 are on the same side of the main air outlet 43. The first secondary air inlet 44 and the second secondary air inlet 47 are next to the main air outlet 43.

Figure 5:
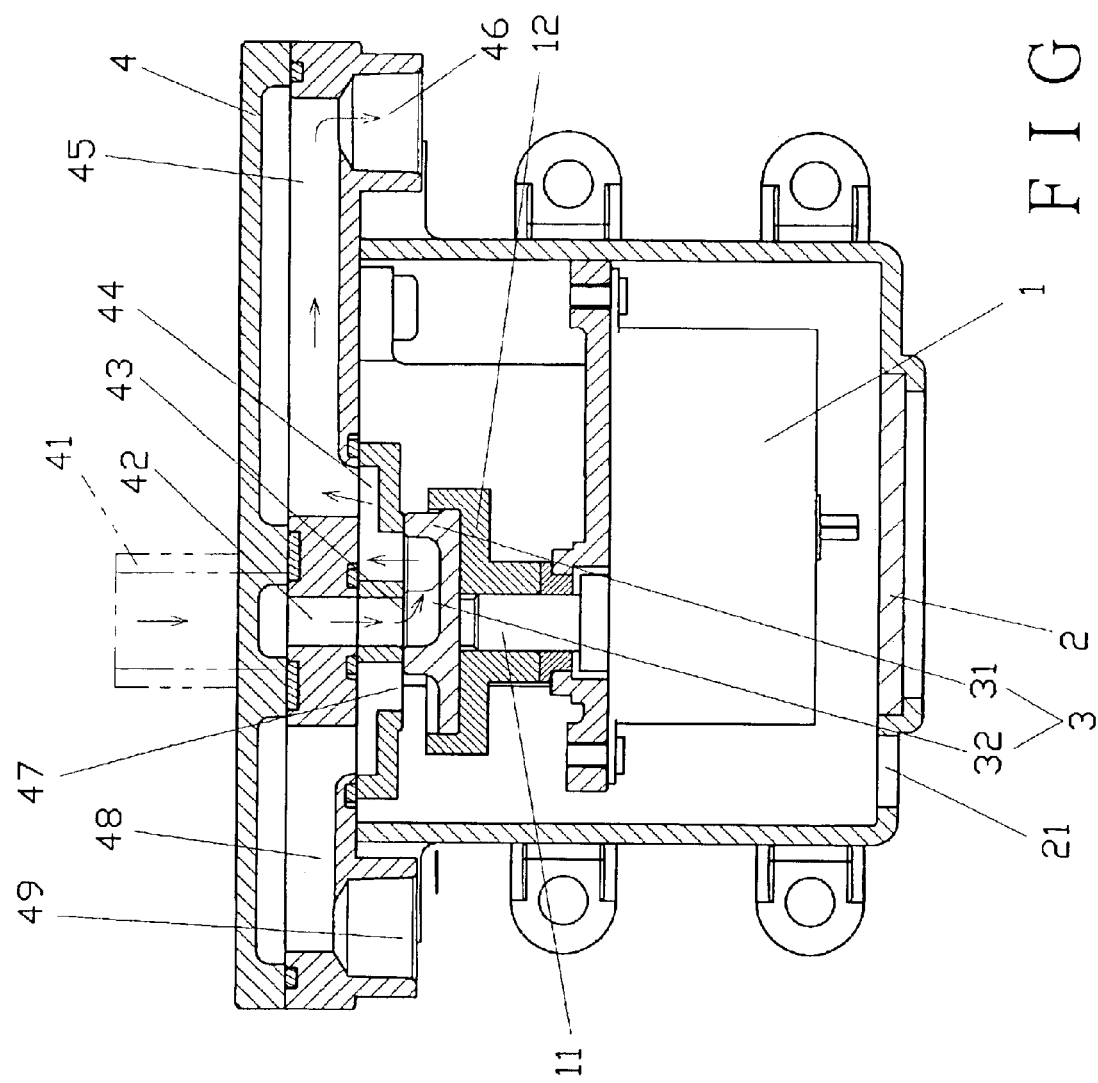
FIG. 5 is a view similar to FIG. 3, showing air flowing through a first secondary air passage.
Figure 6:
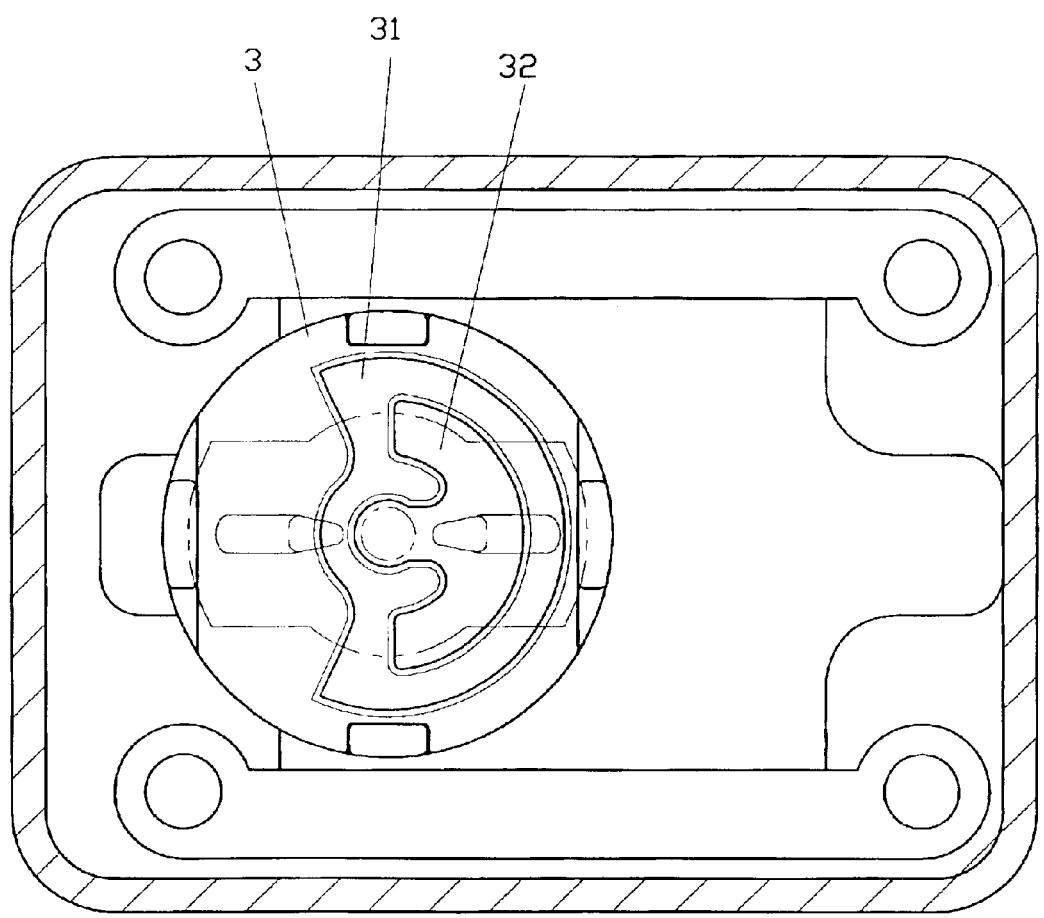
FIG. 6 is another view showing air flowing through the first secondary air passage.
Figure 7:
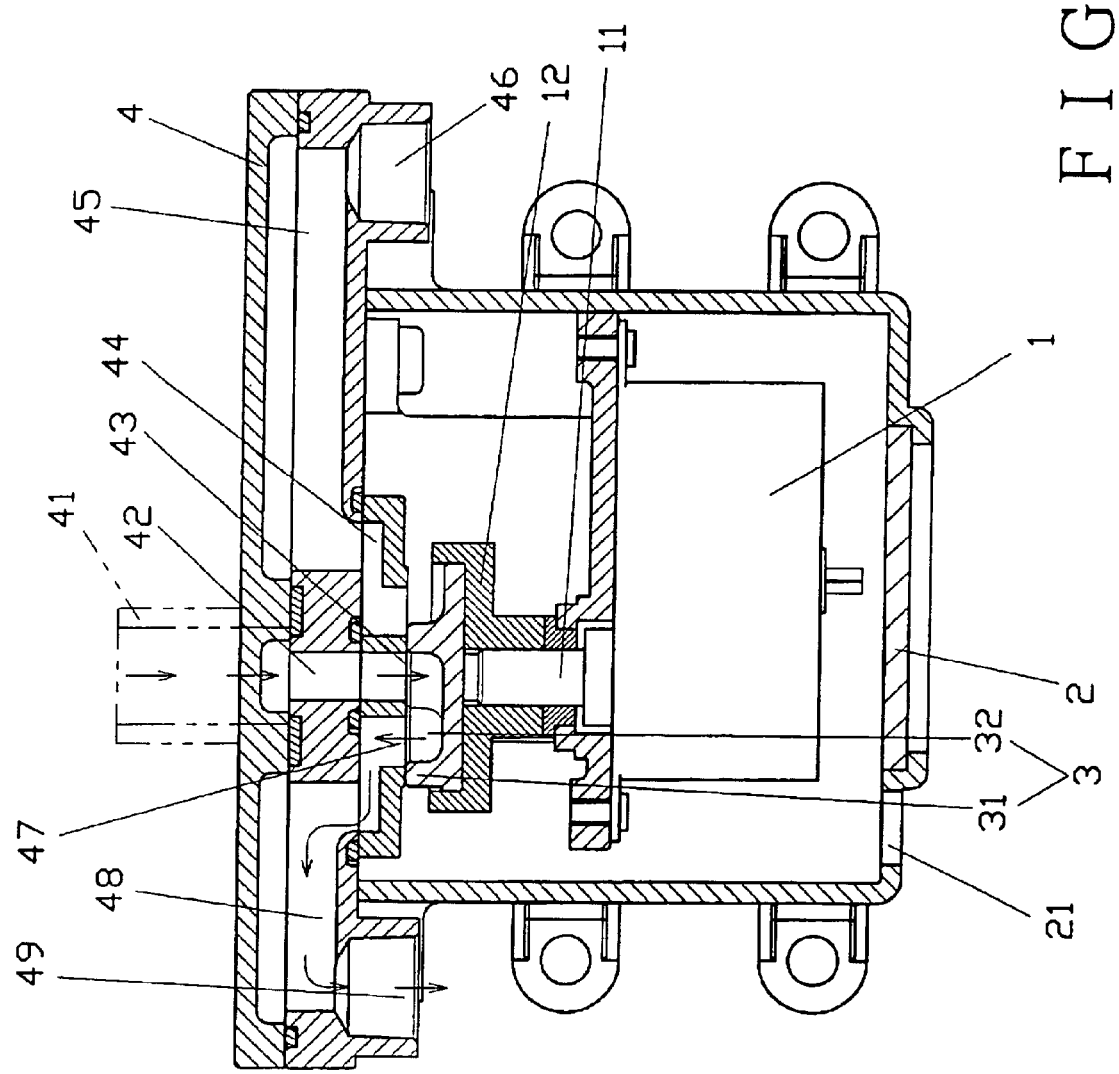
FIG. 7 is a view similar to FIG. 3, showing air flowing through a second secondary air passage.
Figure 8:
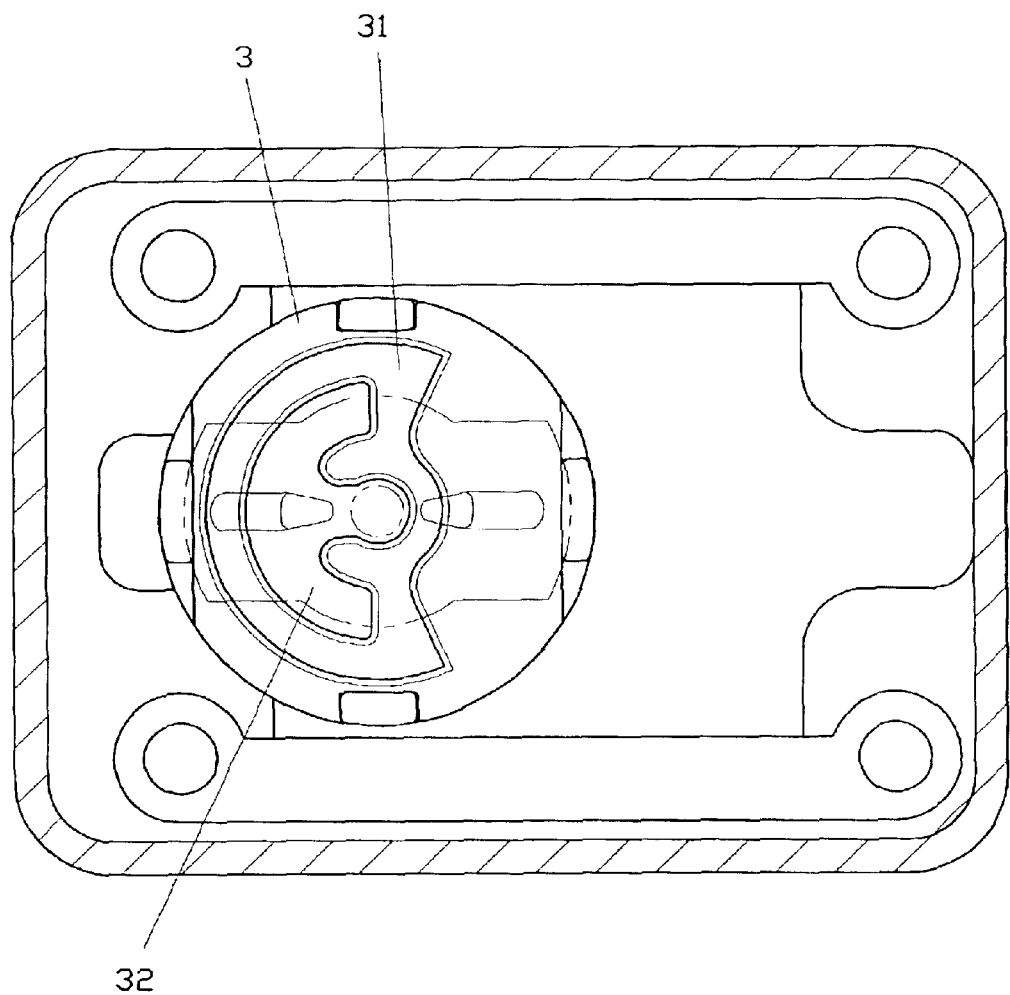
FIG. 8 is another view showing air flowing through the second secondary air passage.
Figure 9:
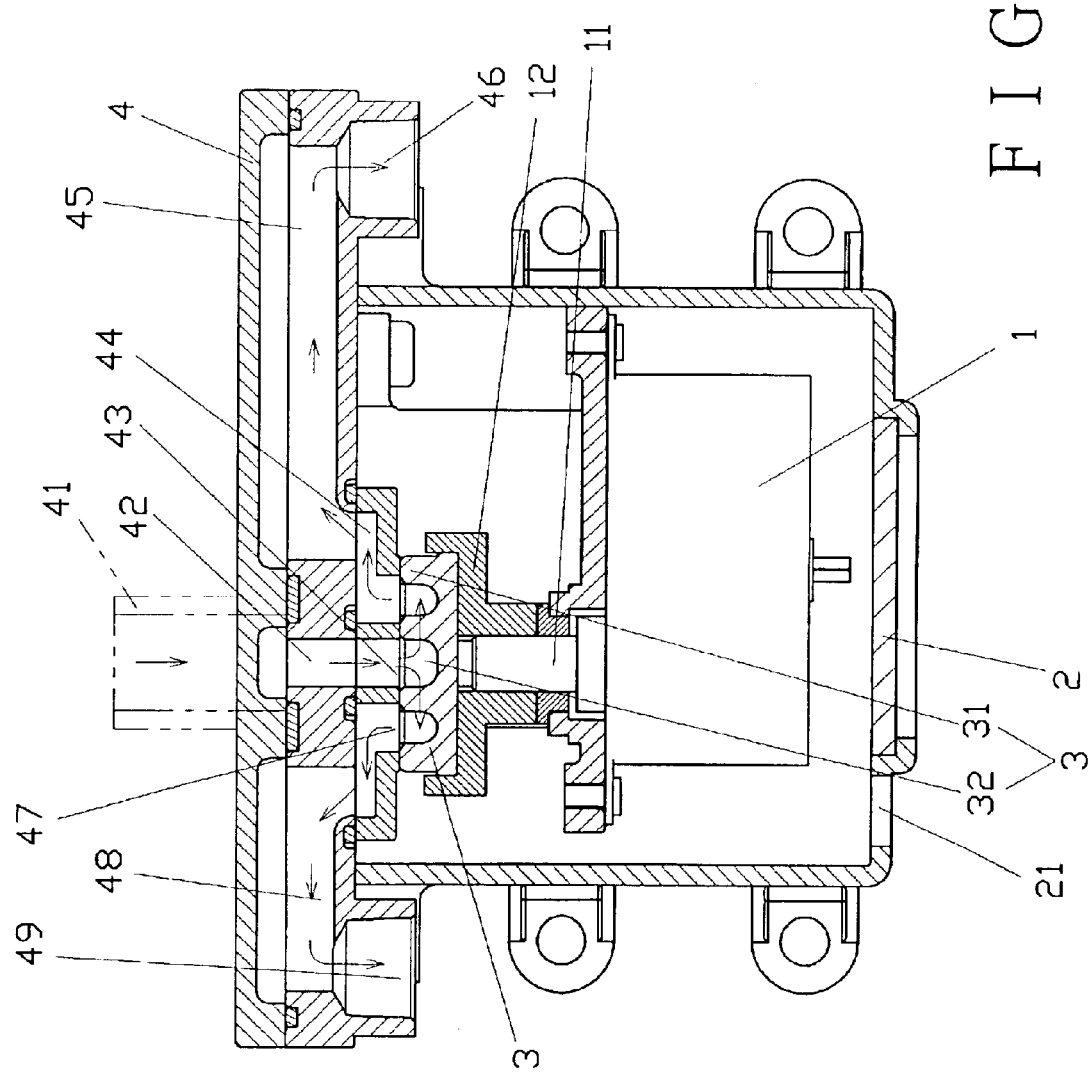
FIG. 9 is a view similar to FIG. 3, showing air flowing through both the first secondary air passage and the second secondary air passage.
Figure 10:
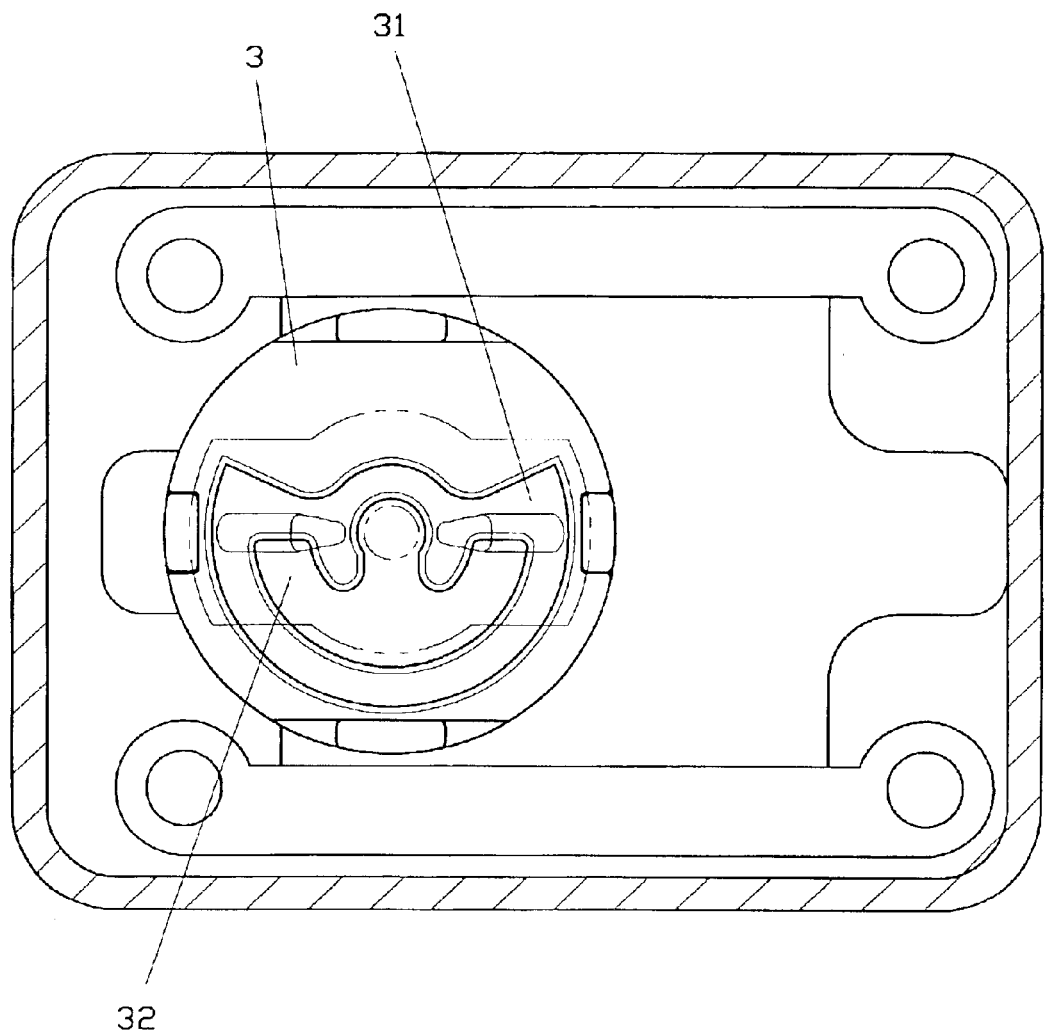
FIG. 10 is another view showing air flowing through both the first secondary air passage and the second secondary air passage.

When the motor 2 is activated, as shown in FIGS. 5 through 10, the valve 3 is driven to turn, which brings the recess 32 of the valve 3 to spin. This brings the recess 32 to align with the first secondary air inlet 44, the second secondary air inlet 47, and the main air outlet 43, sequentially. When in the first sequence of the above, the main air outlet 43 is connected with the first secondary air inlet 44, and blocks the second secondary air inlet 47, as shown in FIGS. 5 and 6. When in the second sequence, the main air outlet 43 is connected with the second secondary air inlet 47, and blocks the first secondary air inlet 44, as shown in FIGS. 7 and 8. When the third sequence is reached, the main air outlet 43 connects with both of the first secondary air inlet 44 and the second secondary air inlet 47, as shown in FIGS. 9 and 10.

In such a way, along with a pair of oxygen filters that connect to the first secondary air inlet 44 and the second secondary air inlet 47, respectively (which is a prior art, and therefore doesn't shown in the drawing), is able to circulate fresh air and to expel waste gas, and maintain at least an oxygen filter working constantly.

I claim:

1. A revolving valve for an oxygen machine comprising a motor, a cage, a valve and an air box, wherein said motor comprising a driving shaft connected to a driven disc which drives said valve;

said cage comprising an air outlet and said motor being secured in said cage;

said valve comprising a sealed rib with a recess inwardly in a semicircular shape;

said air box comprising a main air inlet, a main air passage, a main air outlet, a first secondary air inlet, a first secondary air passage, a first secondary air outlet, a second secondary air inlet, a second secondary air passage, a second secondary air outlet, wherein said main air inlet, said first secondary air passage and said second secondary air passage being isolated within said air box; said main air inlet, said main air passage, and said main air outlet being interconnected with each other; said main air inlet being in one side of said air box while said main air outlet being in another side of said air box; said first secondary air inlet, said first secondary air passage and said first secondary air outlet being interconnected, and said second secondary air inlet, said second secondary air passage, and said second secondary air outlet being interconnected with each other; said first secondary air inlet, said first secondary air outlet, said second secondary air inlet, and said second secondary air outlet being located in the same side of said main air outlet, and said first secondary air inlet and said second secondary air inlet being located immediate next to said main air outlet;

upon said motor being activated, said valve being driven to rotate, this bringing said recess to spin simultaneously and to align with said first secondary air inlet, said second secondary air inlet, and said main air outlet in sequence, connecting said main air outlet with said first secondary air inlet and isolating said second secondary air inlet, or to connect said main air outlet with said second secondary air inlet and isolating said first secondary air inlet, or to connect said main air outlet with both said first secondary air inlet and said second secondary air inlet.

\* \* \* \* \*